United States Patent
Pham-Schoenwetter et al.

(10) Patent No.: US 10,099,999 B2
(45) Date of Patent: Oct. 16, 2018

(54) METHOD FOR SYNTHESIZING 1,1-DIAMINO-2,2-DINITROETHYLENE (FOX-7) OR A SALT THEREOF

(71) Applicant: DIEHL DEFENCE GMBH & CO. KG, Ueberlingen (DE)

(72) Inventors: Oliver Pham-Schoenwetter, Lauf (DE); Bjoern Donner, Adelsdorf (DE); Arno Hahma, Henfenfeld (DE)

(73) Assignee: Diehl Defence GmbH & Co. KG, Ueberlingen (DE)

( * ) Notice: Subject to any disclaimer, the term of this patent is extended or adjusted under 35 U.S.C. 154(b) by 0 days.

(21) Appl. No.: 15/636,931

(22) Filed: Jun. 29, 2017

(65) Prior Publication Data

US 2018/0002269 A1    Jan. 4, 2018

(30) Foreign Application Priority Data

Jun. 29, 2016  (DE) .................. 10 2016 007 865

(51) Int. Cl.
  *C07C 209/68* (2006.01)
  *C07C 209/60* (2006.01)

(52) U.S. Cl.
  CPC .......... *C07C 209/68* (2013.01); *C07C 209/60* (2013.01)

(58) Field of Classification Search
  None
  See application file for complete search history.

(56) References Cited

U.S. PATENT DOCUMENTS 6,312,538 B1   11/2001   Latypov et al.
2012/0178968 A1   7/2012   Goh et al.

FOREIGN PATENT DOCUMENTS

WO   9903818 A1   1/1999

OTHER PUBLICATIONS

Lochert, Ian J: "FOX-7—A New Insensitive Explosive", DSTO-TR-1238, DSTO Aeronautical and Maritime Research Laboratory, Australia, Nov. 2001.
Organic Reaction Mechanism 1971: An annual survey covering the literature dated Dec. 1970 through Nov. 1971, B. Capon, C.W. Rees, John Wiley & Sons, 2008-04-30, ISBN: 0-471-13472-4, p. 426.
Grakauskas et al., "Dinitromethane1", J. Org. Chem, vol. 43, No. 18, 1978, pp. 3485-3488.
Feuer et al., "A New Preparation of Potassium Dinitromethane and its Conversion to 2,2-Dinitro-1,3-propanedio11,2", J. Am. Chem. Soc., vol. 73, p. 1360, 1951.
Jakubowski, "Biochemistry Online—Chapter 2—Protein Structure, A: Amino Acids", Feb. 17, 2016, pp. 1-5.

(Continued)

*Primary Examiner* — Clinton A Brooks
*Assistant Examiner* — Jennifer C Sawyer
(74) *Attorney, Agent, or Firm* — Laurence A. Greenberg; Werner H. Stemer; Ralph E. Locher

(57) ABSTRACT

In a method for synthesizing 1,1-diamino-2,2-dinitroethylene (FOX-7) or a salt thereof, an isourea derivative cation, which consists of a $C(NH_2)(NH_2^+)$ radical and a nucleofugal leaving group bonded to the carbon atom of the $C(NH_2)(NH_2^+)$ radical, is reacted with a dinitromethane anion. The reaction of the isourea derivative cation with the dinitromethane anion takes place in a solution.

9 Claims, 3 Drawing Sheets

(56) References Cited

OTHER PUBLICATIONS

Anniyappan, M., et al., "Synthesis, characterization and thermolysis of 1,1-diamino-2,2-dinitroethylene (FOX-7) and is salts". High Energy Materials Research Laboratory (HEMRL), Pune 411 021, India, Journal of Hazardous Materials B137, 2006, 812.

Holmgren, E., et al., "Energetic Materials", Reactions of Propellants, Explosives and Pyrotechnics, 34th International Annual Conference of ICT Jun. 24, Jun. 27, 2003, Karlsruhe, Federal Republic of Germany.

METHOD FOR SYNTHESIZING 1,1-DIAMINO-2,2-DINITROETHYLENE (FOX-7) OR A SALT THEREOF

CROSS-REFERENCE TO RELATED APPLICATION

This application claims the priority, under 35 U.S.C. § 119, of German application DE 10 2016 007 865.0, filed Jun. 29, 2016; the prior application is herewith incorporated by reference in its entirety.

BACKGROUND OF THE INVENTION

Field of the Invention

The invention relates to the synthesis of 1,1-diamino-2,2-dinitroethylene (FOX-7) or a salt thereof. Various methods are known for synthesizing FOX-7.

1. Nitration of a Nitrogen Heterocycle with Subsequent Hydrolysis to the end Product The synthesis is shown schematically in FIG. 1. The nitrogen heterocycle may be, for example, methylimidazole 3. Nitration thereof with $HNO_3/H_2SO_4$ leads to the formation of an intermediate 4 by nitration of the methyl group and an oxidation of the two carbon atoms of the imidazole ring not involved in bonding to the methyl group. The intermediate 4 decomposes partially at room temperature to a further intermediate 5, wherein FOX-7 1 is formed from both intermediates 4, 5 by hydrolysis in liquid ammonia. The problem in this synthesis is that the further intermediate 5 is very sensitive and readily explodes. Furthermore, the nitration reaction is comparatively inefficient. This results in a low overall yield of typically at most 13%.

2. Nitration of 2-methyl-2-methoxyimidazoledione (6)

The reaction is shown schematically in FIG. 2. The 2-methyl-2-methoxyimidazoledione 6 can be prepared by condensation of the compound 7 with acetamidine hydrochloride 8 in the presence of sodium methoxide in methanol. The nitration of 2-methyl-2-methoxyimidazoledione 6 typically enables an overall yield of up to 38%. A disadvantage of the method is that the resulting intermediate 9 is sensitive and readily explodes and that heat of reaction is formed during the reaction. Therefore, for safety reasons, the reaction must be carried out at high dilution. Comparatively large reaction vessels are thus required, whereby an industrial scale synthesis is uneconomic.

3. Nitration of 2-methyl-4,6-pyrimidinedione (10)

The method is shown schematically in FIG. 3. 2-Methyl-4,6-pyrimidinedione can be prepared from diethyl malonate 11 and acetamidine hydrochloride 8. The yield is around 80%. On hydrolysis of the nitrated intermediate 12, potassium dinitromethanate 13 is formed as by-product. Since potassium methanate is explosive and temperature-sensitive, it is necessary to carry out the nitration slowly and in a temperature-controlled manner. Conducting the reaction on an industrial scale is therefore comparatively expensive. After completion of the nitration, the potassium dinitromethanate 13 is removed by filtration.

Since FOX-7 is comparatively expensive up till now, it has found hardly any industrial application to date apart from in small amounts as booster charge in nuclear warheads, igniters and ignition enhancers. Due to its high performance and low sensitivity to shock, friction and thermal influences, FOX-7 would be attractive for many applications as a high-performance explosive, if it were more convenient to prepare. For example, it could be used in diverse applications as a less sensitive performance enhancer for spectral flares in decoy targets, as performance enhancer in propellants and as main charge. The object of the present invention, therefore, is to provide an alternative method for the cost-effective preparation of FOX-7.

SUMMARY OF THE INVENTION

A method for synthesizing 1,1-diamino-2,2-dinitroethylene (FOX-7) or a salt thereof is provided in accordance with the invention, wherein an isourea derivative cation is reacted with a dinitromethane anion. The isourea derivative cation here consists of a $C(NH_2)(NH_2^+)$ radical and a nucleofugal leaving group bonded to the carbon atom of the $C(NH_2)(NH_2^+)$ radical. The reaction of the isourea derivative cation with the dinitromethane anion takes place in a solution. The reaction can be carried out in particular in a polar aprotic solvent, such as dimethylformamide (DMF) for example.

In the reaction of the isourea derivative cation, a nucleophilic substitution of the leaving group by the dinitromethane anion takes place. By means of the nucleophilic leaving group bonded to the $C(NH_2)(NH_2^+)$ radical, the isourea derivative is activated. Since the leaving group is nucleofugal, the isourea derivative in the nucleophilic substitution reaction is the electrophile.

The method according to the invention is considerably more cost-effective to carry out than the syntheses known from the prior art. This is because, inter alia, the method is substantially less dangerous to carry out since no hazardous nitration step is carried out and the reaction proceeds at a comparatively low temperature in solution. The product can be precipitated from the solution and be filtered off. A salt of FOX-7 is primarily formed in the reaction which can be converted into FOX-7 by acidification or neutralization of the or a solution containing the salt. Since the synthesis proceeds at a relatively low temperature, the use of the sensitive and explosive dinitromethane anion does not present a safety problem.

The nucleofugal leaving group may be an O-alkyl, in particular O-methyl, O-ethyl, O-propyl, O-butyl or O-pentyl, triazolyl, halide, in particular chloride, carbonyl halide, in particular carbonyl chloride, nonaflate, trifluoromethanesulphate, sulphonate, in particular halosulphonate, in particular fluorosulphonate, tosyl, mesyl, diazonium, oxonium, quaternary ammonium compound, ester, acid anhydride, nitrate, phosphate, organic ester, ammonium, phenol, alcohol or a carboxylic radical. The O-alkylated isourea derivatives have a high reactivity due to the alkylation at the carbonyl oxygen of the urea since the O-alkyl group is a readily cleavable leaving group.

An alternative leaving group is a halide, a chloride for example. For example, the isourea derivative cation can be present as chloroformamidinium hydrochloride, which may be prepared, for example, by anhydrous hydrochlorination of cyanamide. In this case, a hydrochloride adduct is formed with a chlorine leaving group on the amidinium carbon.

A further, very suitable leaving group is a triazolyl radical. An isourea derivative cation having this leaving group is present, for example, in commercially available triazolecarboxamidine hydrochloride.

Accordingly, the isourea derivative cation may be a chloroformamidinium ion or a triazole carboxamidine ion. The chloroformamidinium ion or the triazole carboxamidine ion may be associated with chloride as counterion. In principle, the isourea derivative cation can be associated with a sulphate, hydrogen sulphate, acetate or halide, particularly chloride, as counterion.

The dinitromethane anion may be associated with a potassium ion or ammonium ion as counterion.

A 1,1-diamino-2,2-dinitroethylene anion formed in the synthesis may be converted into 1,1-diamino-2,2-dinitroethylene by lowering the pH of the/a solution containing the 1,1-diamino-2,2-dinitroethylene anion. The solution can be the solution in which synthesis has been carried out. It is also possible, however, to separate the 1,1-diamino-2,2-dinitroethylene anion in the form of a salt from the solution in which the synthesis has been carried out, and then the salt is dissolved in the same or another solvent to form the solution mentioned.

Other features which are considered as characteristic for the invention are set forth in the appended claims.

Although the invention is illustrated and described herein as embodied in a method for synthesizing 1,1-diamino-2,2-dinitroethylene (fox-7) or a salt thereof, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
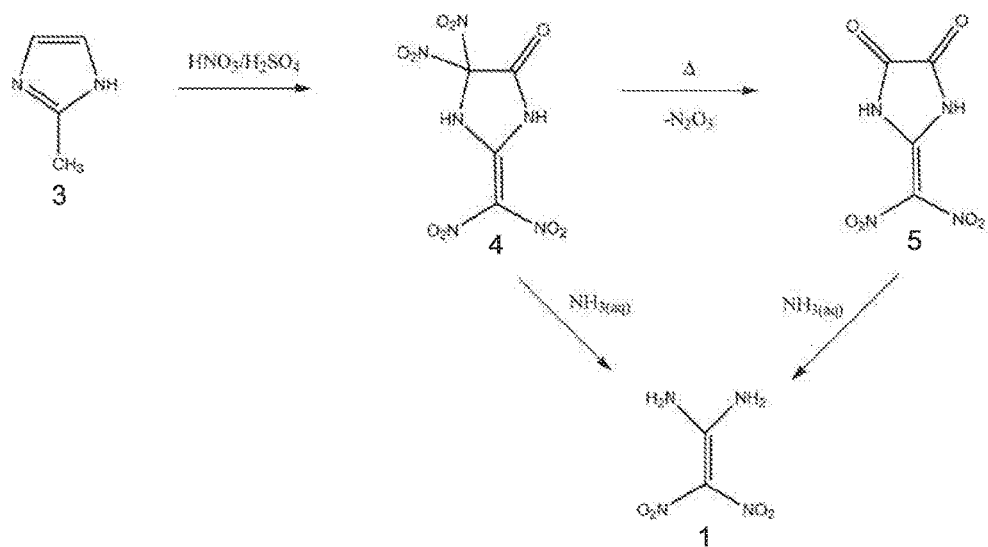
FIG. 1 shows a reaction scheme of a synthesis of FOX-7 from nitration of a nitrogen heterocycle with subsequent hydrolysis to an end product.
Figure 2:
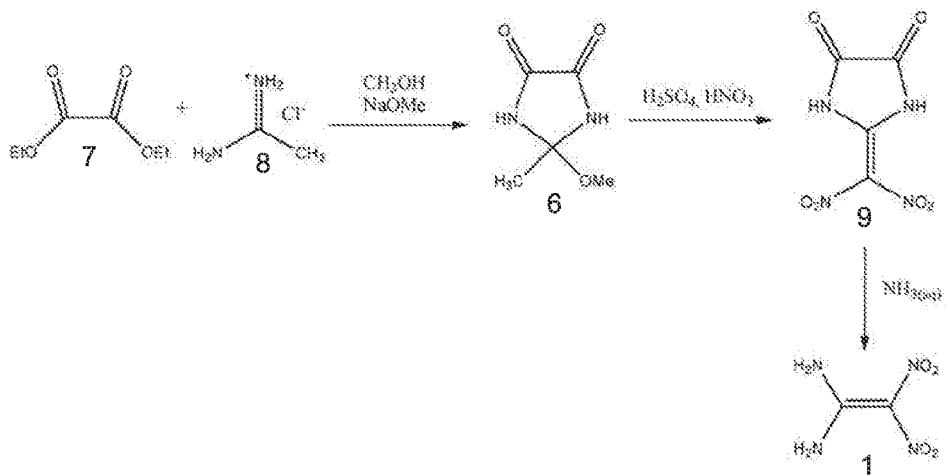
FIG. 2 shows a reaction scheme of a synthesis of FOX-7 from nitration of 2-methyl-2-methoxyimidazoledione.
Figure 3:
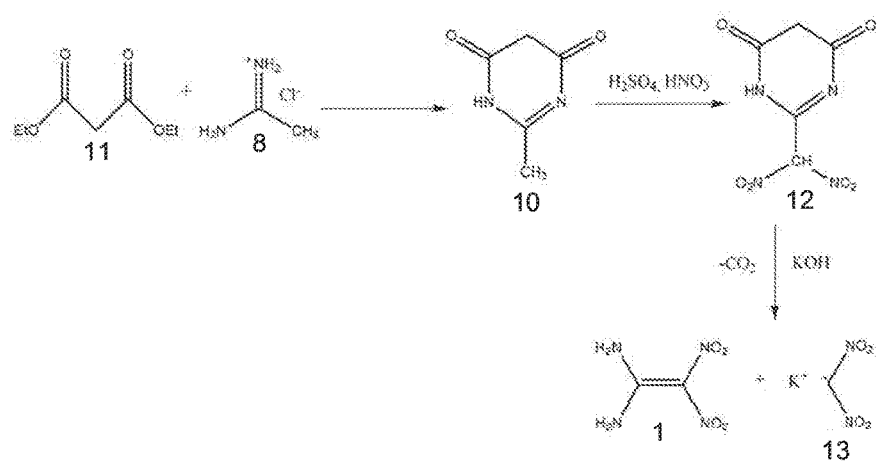
FIG. 3 shows a reaction scheme of a synthesis of FOX-7 from nitration of 2-methyl-4,6-pyrimidinedione.
Figure 4:
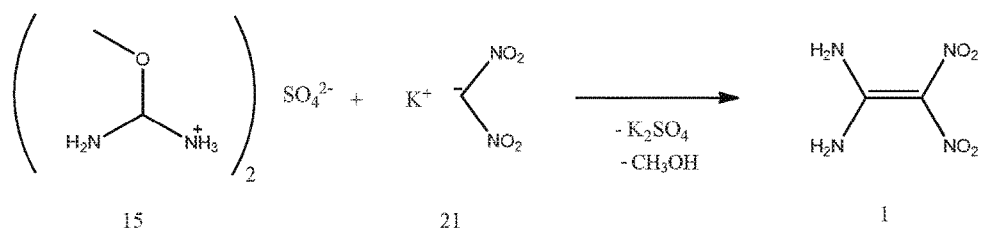
FIG. 4 shows a reaction scheme of the synthesis of FOX-7 from O-alkylated isourea salt.

To synthesize FOX-7 from O-alkylated isourea salt according to FIG. 4, 490 mg (3.4 mmol) of potassium dinitromethanate and 419 mg (3.4 mmol) of O-methylisourea sulphate are dissolved successively with stirring in 50 ml of water at 70° C. in a 100 ml round-bottomed flask. The solution is then further stirred at 70° C. for one hour. The white precipitate formed is separated off by filtration. From the remaining solution, the solvent is slowly distilled off in the rotary evaporator. The FOX-7 product precipitates here as a yellow precipitate. For further purification, the product is dissolved in acetonitrile/methanol 30/70 and subjected to chromatography on a 20 cm long silica column with acetonitrile/methanol 30/70 as eluent mixture. From the fraction comprising the product, the solvent is distilled off by means of a rotary evaporator.

A 1H-NMR spectrum, a 13C-NMR spectrum and a mass spectrum of the reaction product and a KFOX-7 reference show that FOX-7 is indeed present in the reaction. The results of the analysis of the reaction product compared to the KFOX-7 reference are reported in Table 1 below:

TABLE 1

| Analysis | Reaction product | KFOX-7 reference |
| --- | --- | --- |
| 1H-NMR (400 MHz) | 8.4 ppm (s) broad | 8.8 ppm (s) broad (corresponds to FOX-7) |
| 13C-NMR (400 MHz) | 158.43 ppm singlet | 158.41 ppm singlet |
| Mass spectrum (ESI) | 149 m/z | 149 m/z |

Figure 5:
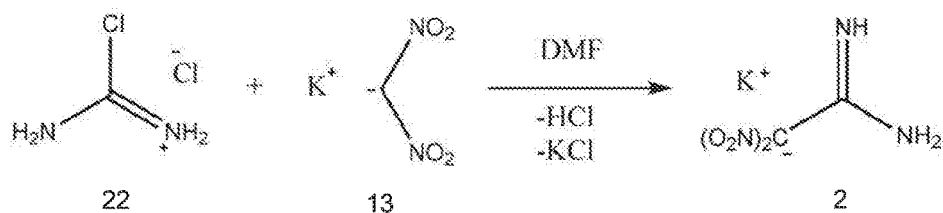
FIG. 5 shows a reaction scheme of the synthesis of KFOX-7 from chloroformamidinium hydrochloride.

To synthesize KFOX-7 in accordance with the reaction scheme according to FIG. 5, 73 mg (0.5 mmol) of potassium dinitromethanate is dissolved in 20 ml of DMF at 60° C. in a 50 ml glass beaker and 58 mg (0.5 mmol) of chloroformamidinium hydrochloride are added. The solution was stirred at 60° C. for 2 hours and then allowed to cool to room temperature with stirring. After distilling off the solvent, the residue was dried in an explosion-proof drying oven at 50° C. and then measured thermoanalytically by dynamic differential scanning calorimetry (DSC) and also by IR, NMR and mass spectroscopy. The result is shown in Table 2 below:

TABLE 2

| Analysis | Reaction product | K-FOX-7 reference |
| --- | --- | --- |
| 1H-NMR (400 MHz) | 8.54 ppm (s) | 8.88 ppm (s) (corresponds to FOX-7) |
| 13C-NMR (400 MHz) | 158.4 ppm | 158.4 ppm (KFOX-7) |
| Mass spectrum | 149 m/z (=M + 1 peak FOX-7) | 148 m/z |
| DSC | 230° C. | 220-250° C. (FOX-7) |

Comparison with the KFOX-7 reference shows that the reaction product comprises KFOX-7.

Figure 6:
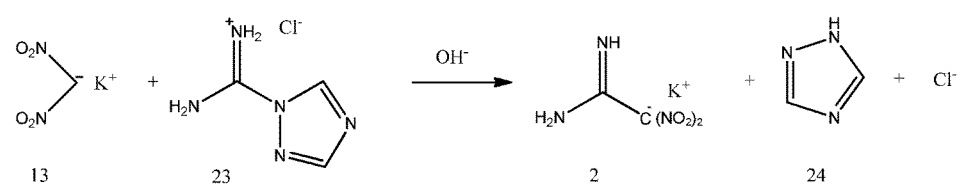
FIG. 6 shows a reaction scheme of the synthesis of KFOX-7 from triazole carboxamidine hydrochloride.

To synthesize KFOX-7 according to the reaction scheme shown in FIG. 6, 980 mg of potassium dinitromethanate (6.8 mmol) are dissolved in 10 ml of distilled water in a 100 ml round-bottomed flask. To this is added 1 g of 1H-1,2,4-triazole-1-carboxamidine hydrochloride (6.8 mmol). Immediately after the addition, the pH is adjusted with 20% KOH solution to pH 11 to 12 and the temperature is increased to 50° C. The solution is stirred overnight at 50° C. The solvent is then distilled off in the rotary evaporator. A yellow residue remains which is washed in a filter frit three times with 20 ml of isopropanol each time to remove triazole and KOH. Determination of the decomposition temperature by DSC gives a value of 222° C., which is in agreement with the value of the KFOX-7 reference. A 13C-NMR spectrum shows a peak for KFOX-7 which is identical to the KFOX-7 peak of a reference sample. A mass spectrometric investigation also shows agreement of the reaction product with the KFOX-7 reference. The results are shown in Table 3 below.

TABLE 3

| Analysis | Reaction product | KFOX-7 reference |
|---|---|---|
| 13C-NMR | 158.4 ppm singlet | 158.41 ppm singlet |
| Mass spectrum | 149 m/z | 149 m/z |
| DSC | 228° C. | 228° C. |

Comparison with the KFOX-7 reference shows that the reaction product comprises KFOX-7.

In the working examples, it is also possible to use ammonium dinitromethanate in place of potassium dinitromethanate.

The invention claimed is:

1. A method for synthesizing 1,1-diamino-2,2-dinitroethylene (FOX-7) or a salt thereof, which comprises the step of:
reacting an isourea derivative cation, which consists of a $C(NH_2)(NH_2^+)$ radical and a nucleofugal leaving group bonded to a carbon atom of the $C(NH_2)(NH_2^+)$ radical, with a dinitromethane anion.

2. The method according to claim 1, which further comprises performing the reacting of the isourea derivative cation with the dinitromethane anion in a polar aprotic solvent.

3. The method according to claim 2, which further comprises using dimethylformamide (DMF) as the polar aprotic solvent.

4. The method according to claim 1, which comprises selecting the nucleofugal leaving group from the group consisting of an O-alkyl, O-methyl, O-ethyl, O-propyl, O-butyl, O-pentyl, triazolyl, halide, chloride, carbonyl halide, carbonyl chloride, nonaflate, trifluoromethanesulphate, sulphonate, halosulphonate, fluorosulphonate, tosyl, mesyl, diazonium, oxonium, quaternary ammonium compound, ester, acid anhydride, nitrate, phosphate, organic ester, ammonium, phenol, alcohol and a carboxylic radical.

5. The method according to claim 1, which further comprises selecting the isourea derivative cation from the group consisting of a chloroformamidinium ion and a triazole carboxamidine ion.

6. The method according to claim 1, wherein the isourea derivative cation is associated with a sulphate, hydrogen sulphate, acetate, halide, or chloride, as a counterion.

7. The method according to claim 5, wherein the isourea derivative cation is associated with chloride as a counterion.

8. The method according to claim 1, wherein the dinitromethane anion is associated with a potassium ion or ammonium ion as a counterion.

9. The method according to claim 1, which further comprises converting a 1,1-diamino-2,2-dinitroethylene anion formed in a synthesis into the 1,1-diamino-2,2-dinitroethylene by lowering a pH of a solution containing the 1,1-diamino-2,2-dinitroethylene anion.

* * * * *